United States Patent [19]

Leach

[11] 4,290,924
[45] Sep. 22, 1981

[54] CATALYST COMPOSITION USEFUL FOR PREPARING 2,6-XYLENOL

[75] Inventor: Bruce E. Leach, Ponca City, Okla.

[73] Assignee: Conoco, Inc., Ponca City, Okla.

[21] Appl. No.: 137,195

[22] Filed: Apr. 4, 1980

Related U.S. Application Data

[62] Division of Ser. No. 45,571, Jun. 4, 1979, Pat. No. 4,227,024.

[51] Int. Cl.$^3$ ........................ B01J 23/78; B01J 23/82; B01J 23/86
[52] U.S. Cl. .................................................... 252/469
[58] Field of Search ................................ 252/469, 470

[56] References Cited

U.S. PATENT DOCUMENTS 3,953,529  4/1976  Yonemitsu et al. ................ 568/804
4,024,195  5/1977  Yonemitsu et al. ................ 568/781

FOREIGN PATENT DOCUMENTS 47-18739  5/1972  Japan ................................ 568/804

Primary Examiner—W. J. Shine
Attorney, Agent, or Firm—Bayless E. Rutherford, Jr.

[57] ABSTRACT

A process for preparing 2,6-xylenol in high selectivity and a catalyst composition useful therein are disclosed. The process comprises reacting phenol, o-cresol or mixtures thereof with methanol in presence of water, hydrogen and a catalyst consisting essentially of $Fe_2O_3$, $SnO_2$, $Cr_2O_3$, and $K_2O$.

5 Claims, No Drawings

CATALYST COMPOSITION USEFUL FOR PREPARING 2,6-XYLENOL

CROSS-REFERENCE TO RELATED APPLICATIONS

This application is a division of application Ser. No. 45,571, filed June 4, 1979, now U.S. Pat. No. 4,227,024.

FIELD OF THE INVENTION

The invention is in the general field of processes for preparing 2,6-xylenol by alkylation of phenol or o-cresol and a catalyst composition useful therein.

GENERAL BACKGROUND 2,6-Xylenol is used to prepare polyphenylene oxide which has utility as an engineering plastic.

Many catalysts are known for the preparation of 2,6-xylenol by the ortho-alkylation of phenol. For example, U.S. Pat. Nos. 3,972,836 and 4,041,085 teach the use of magnesium oxide. German publication No. 2,704,440 teaches the use of calcium oxide. German publication No. 2,716,035 teaches the use of copper chromite alone or in combination with MnO, ZnO, $Al_2O_3$, or $MnO_2$. U.S. Pat. No. 4,024,195 teaches the use of a combination of $Fe_2O_3/SiO_2/Cr_2O_3/K_2O$. U.S. Pat. No. 3,790,641 teaches the use of the following oxide components: Mg-Ce-Sn-V; Ce-Sc-Sn; La-Y-Sn.

The MgO based catalysts have the disadvantage of requiring a high temperature (e.g. 475°-525° C.): additionally, they have a lower selectivity as compared to the catalyst used in the present invention. Iron oxide based catalysts alone have very low activity. Use of vanadium oxide in combination with iron oxide improves the activity but results in high methanol decomposition. The $Fe_2O_3/SiO_2/Cr_2O_3/K_2O$ catalyst works well but results in the formation of an undesirable amount of BTX (benzene, toluene, xylenes). The catalyst of my invention, as compared to the aforementioned catalyst, has the advantage of having a higher selectivity in preparation of 2,6-xylenol and the production of less BTX.

BRIEF SUMMARY OF THE INVENTION

In one aspect, the present invention is directed to a process for preparing 2,6-xylenol in high selectivity by reacting phenol, o-cresol, or mixtures thereof, with methanol in the presence of water, and, optionally, hydrogen, using a catalyst consisting essentially of $Fe_2O_3$, $SnO_2$, $Cr_2O_3$ and $K_2O$.

In another aspect, the present invention is directed to a catalyst composition which consists essentially of a major amount of $Fe_2O_3$ and minor amounts of $SnO_2$, $Cr_2O_3$ and $K_2O$.

DETAILED DESCRIPTION

The Catalyst Composition

The catalyst composition of my invention contains a major amount of $Fe_2O_3$ and minor amounts of $SnO_2$, $Cr_2O_3$ and $K_2O$. Suitable and preferred amounts of the various components are shown in the following table, in weight percent.

| Component | Suitable | Preferred |
|---|---|---|
| $Fe_2O_3$ | 90-97 | 93-96 |
| $SnO_2$ | 0.5-5 | 1-3 |
| $Cr_2O_3$ | 0.5-5 | 1-3 |
| $K_2O$ | 0.01-1 | 0.02-0.5 |

While the amounts shown in the table can provide totals above 100 it is to be understood that use of a larger amount of one or more components will require a lesser amount of the other components so that the total amount is not above 100.

Knowing the various components used in the catalyst composition of my invention any person skilled in the art, without undue experimentation, can readily prepare the composition. In order to provide a more complete disclosure a description will be provided of a typical means of preparing the composition.

Suitable materials for use in preparing the catalyst composition are shown below.

| Component | Source Acceptable |
|---|---|
| $Fe_2O_3$ | Ferric Nitrate - $Fe(NO_3)_3 \cdot 9H_2O$ |
|  | Ferric Sulfate - $Fe_2(SO_4)_3 \cdot 9H_2O$ |
| $SnO_2$ | Tin (IV) Nitrate |
|  | Tin (II) Acetate |
|  | Tin (II) Chloride |
|  | Tin (IV) Chloride |
| $Cr_2O_3$ | Chromium Nitrate - $Cr(NO_3)_3 \cdot 9H_2O$ |
|  | Chromium Acetate - $Cr(C_2H_3O_2)_3 \cdot H_2O$ |
|  | Chromium Oxalate - $Cr_2(C_2O_4)_3 \cdot 6H_2O$ |
|  | Chromium Sulfate - $Cr_2(SO_4)_3 \cdot 18H_2O$ |
|  | Chromium Chloride - $CrCl_3 \cdot 6H_2O$ |
| $K_2O$ | KOH, $K_2CO_3$, Potassium Acetate, Potassium Oxalate |

The iron, chromium and tin components are dissolved in water (temperature can be 20°-90° C., but preferably is 60°-80° C.). Precipitation can be effected with ammonia, sodium carbonate or sodium hydroxide. The precipitation step should be slow (requiring about 1 hour). The precipitate should be aged at least 1 hour before filtration and washing. It is then dried in air at 110°-180° C. The potassium component is then added, following which the composition is dried and calcined at 470°-600° C. for 1 to 6 hours, preferably for 2-3 hours, at about 500° C. The composition is then screened to a desirable mesh size (8-20 mesh).

When the catalyst is used in the process described herein it is placed in the reactor and reduced with hydrogen gas prior to use. The hydrogen gas is passed over the catalyst at a temperature of 300° to 500° C. at a flow rate of 2 to 6 volumes of hydrogen per minute per volume of reactor for 2 to 12 hours.

THE PROCESS

My process can use phenol, o-cresol or any range of mixtures thereof. Methanol is used in the process with a suitable amount being in the range of about 1 to about 10 moles of methanol per mole of phenol and/or o-cresol. On the same basis the preferred amount of methanol is in the range of about 3 to about 5.

The presence of water is desirable in conducting the process. A suitable amount of water is about 5 to about 15 weight percent, based on the total phenolics and methanol. On the same basis the amount of water is in the range of about 8 to about 12.

It is necessary that the catalyst be treated (i.e. reduced) with hydrogen prior to commencing the process. (This feature has been described in connection with the description of the catalyst.) In some cases it may be desirable to use hydrogen as a co-feed in conducting the process. When hydrogen is used the amount is in the range of 0.5 to 10 volumes per volume of catalyst per minute.

The amount of catalyst used is related to the liquid hourly space velocity as follows $$LHSV = \frac{\text{volume of liquid per hour*}}{\text{volume of catalyst}}$$

*includes phenol and/or o-cresol methanol and water

A suitable range of LHSV is about 0.1 to about 5, with the preferred range being about 0.2–3.

The process is conducted at a temperature in the range of about 380° to 420° C. (Above 420° C. methanol decomposition occurs). Preferably, the temperature is in the range of about 400° to about 415° C.

The reaction is conducted at a pressure from atmospheric to 1,000 psig. Preferably, the pressure is not above 200 psig.

The desired product (i.e. 2,6-xylenol) can be recovered from the reaction products by fractional distillation.

The process of my invention results in a very high selectivity of 2,6-xylenol. Of total alkylated aromatics in the product mixture, the o-cresol and 2,6-xylenol will be at least 99 weight percent. Major impurities are 2,4,6-trimethylphenol, 2,4-xylenol and BTX.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This example illustrates the preparation of the catalyst. 300 g $Fe(NO_3)_3.9H_2O$ and 3 g $Cr(NO_3)_3.9H_2O$ were dissolved in 3000 ml $H_2O$. 3 g of Sn was dissolved in $HNO_3$ and added to the solution. The iron, chromium and tin oxides were precipitated at 25° C. with 20 percent aqueous ammonia to a pH value of 7.0. The precipitate was filtered, washed with water and dried overnight at 140° C. in air. $K_2CO_3$ (17 mg) was added in 30 cc $H_2O$ and the material re-dried at 140° C. It was then calcined in an air atmosphere at 470° C. and crushed and sieved into an 8×20 mesh fraction.

The catalyst had the following composition, in weight percent: $Fe_2O_3$—94.8; $SnO_2$—3; $Cr_2O_3$—2; $K_2O$—0.2.

EXAMPLE 2

20 grams of the catalyst were placed in a ½ inch stainless steel reactor. Hydrogen gas was passed through the reactor at 370° C. at a rate of 200 cc/min for 4 hours.

The feedstock in this example consisted of 1 part phenol, 1 part o-cresol, 2 parts methanol, and 0.2 part water (all by weight). The feedstock was pumped at LHSV=2 through a preheat section at 375° C. and then through the catalyst bed controlled at 400°–410° C.

No plugging of the catalyst was observed.

A run was made on the reactor for 8 consecutive days for a total run time of about 60 hours.

The product was analyzed by GLC.

The results are shown below in Tables I and II.

TABLE I

| Product Analysis | 60 Hours | Cumulative 0–60 Hours |
|---|---|---|
| Methanol, weight % | 8.30 | 9.36 |
| $H_2O$, weight %* | 20.96 | 20.72 |
| Cresylics, weight % | 70.74 | 69.92 |

*Calculated

TABLE II

| Cresylics Distribution | Weight Percent | |
|---|---|---|
| | 60 Hours | Cumulative 0–60 Hours |
| BTX* | 0.15 | 0.16 |
| Anisole | 0.05 | 0.05 |
| Phenol | 5.07 | 7.35 |
| o-Methylanisole | 0.06 | 0.05 |
| o-Cresol | 34.19 | 38.24 |
| 2,6-Xylenol | 59.97 | 53.69 |
| 2,4-Xylenol | 0.06 | 0.05 |
| 2,4,6-TMP | 0.41 | 0.39 |
| High boilers | 0.04 | 0.02 |
| | 100.00 | 100.00 |

*Benzene toluene, xylenes

Additional runs were made using the same conditions except for catalyst. The following catalysts were tested:
Combination of iron and copper
Combination of iron and copper chromite
Combination of iron and $MnO_2$
Combination of iron and CoO
Combination of iron and $V_2O_3$
Combination of iron and $MoO_3$ All of the foregoing catalysts resulted in plugging of the catalyst.

A run was made using the following catalyst $Fe_2O_3/SiO_2/SnO_2/K_2O$. The run had a low activity (2,6-xylenol formation) which decreased rapidly.

Thus, having described the invention in detail, it will be understood by those skilled in the art that certain variations and modifications may be made without departing from the spirit and scope of the invention as defined herein and in the appended claims.

I claim:

1. A catalyst composition consisting essentially of the following materials in percent by weight: $Fe_2O_3$—about 90 to about 97; $SnO_2$—about 0.5 to about 5; $Cr_2O_3$—about 0.5 to about 5; $K_2O$—about 0.01 to about 1.

2. The catalyst composition of claim 1 wherein the materials are present in the following amounts: $Fe_2O_3$—about 93 to about 96; $SnO_2$—about 1 to about 3; $Cr_2O_3$—about 1 to about 3; $K_2O$—about 0.02 to about 0.5.

3. The catalyst composition of claims 1 or 2 characterized further in that it has been treated with hydrogen gas at 300° to 500° C. for 2 to 12 hours at a flow rate of 2 to 6 volumes of hydrogen per minute per volume of reactor.

4. The catalyst composition of claim 1 wherein the materials are present in the following amounts: $Fe_2O_3$—about 94.8; $SnO_2$—about 3; $Cr_2O_3$—about 2; $K_2O$—about 0.2.

5. The catalyst composition of claim 4 characterized further in that it has been treated with hydrogen gas at 370° C. for 4 hours at a rate of 10 cc/min per gram of catalyst.

* * * * *